(12) United States Patent
Waters et al.

(10) Patent No.: US 7,537,584 B2
(45) Date of Patent: *May 26, 2009

(54) CHEMICALLY TANNING HUMAN SKIN

(75) Inventors: Drew Waters, Sachse, TX (US);
Brandon Shaw, Irving, TX (US); Frank Verdun, Franklin, TN (US)

(73) Assignee: Safe Tan, Dallas, TX (US)

( * ) Notice: Subject to any disclaimer, the term of this patent is extended or adjusted under 35 U.S.C. 154(b) by 165 days.

This patent is subject to a terminal disclaimer.

(21) Appl. No.: 10/932,438

(22) Filed: Sep. 2, 2004

(65) Prior Publication Data

US 2005/0113769 A1 May 26, 2005

Related U.S. Application Data

(63) Continuation of application No. 09/595,787, filed on Jun. 16, 2000, now Pat. No. 6,802,830.

(51) Int. Cl.
*A61M 35/00* (2006.01)
*A61K 8/00* (2006.01)
*A61K 8/18* (2006.01)
*A61Q 17/04* (2006.01)

(52) U.S. Cl. .............................. 604/290; 424/59; 424/60

(58) Field of Classification Search ................. 604/289, 604/290; 424/60
See application file for complete search history.

(56) References Cited

U.S. PATENT DOCUMENTS

| 870,766 | A | 11/1907 | Eaton |
|---|---|---|---|
| 1,262,638 | A | 4/1918 | Class |
| 1,982,509 | A | 11/1934 | Frank |
| 2,700,384 | A | 1/1955 | Ivory |
| 2,949,403 | A | 8/1960 | Amdreadis |
| 3,060,097 | A | 10/1962 | Fellows |
| 3,177,120 | A | 4/1965 | Black et al. |
| 3,272,713 | A | 9/1966 | Runge |
| 3,856,934 | A | 12/1974 | Kligman |
| 3,868,950 | A | 3/1975 | Kato |
| 3,920,808 | A | 11/1975 | Fusaro |
| 3,932,151 | A | 1/1976 | Lau |
| 4,231,289 | A | 11/1980 | Domicent |
| 4,453,914 | A | 6/1984 | Huniu et al. |

(Continued)

FOREIGN PATENT DOCUMENTS

BE 814319 5/1974

(Continued)

OTHER PUBLICATIONS

Color Roditne: Dihydroxyacetone, Federal Register, 38: No. 148, p. 20615, Aug. 2, 1973.

(Continued)

*Primary Examiner*—Tatyana Zalukaeva
*Assistant Examiner*—Melanie J Hand
(74) *Attorney, Agent, or Firm*—Thrasher Associates, LLC

(57) ABSTRACT

The invention teaches devices and methods for chemically tanning human skin. It is emphasized that this abstract is provided to comply with the rules requiring an abstract that will allow a searcher or other reader to quickly ascertain the subject matter of the technical disclosure. It is submitted with the understanding that it will not be used to interpret or limit the scope or meaning of the claims.

1 Claim, 4 Drawing Sheets

U.S. PATENT DOCUMENTS

| | | | |
|---|---|---|---|
| 4,453,941 A | 6/1984 | Jacobs | |
| 4,749,130 A | 6/1988 | Utzinger | |
| 4,826,681 A | 5/1989 | Jacquet et al. | |
| 4,832,943 A | 5/1989 | Grollier | |
| 4,874,412 A | 10/1989 | Nowack | |
| 5,073,996 A | 12/1991 | Schinle | |
| 5,089,269 A | 2/1992 | Noda | |
| 5,102,660 A | 4/1992 | Forestier | |
| 5,153,174 A | 10/1992 | Band et al. | |
| 5,232,688 A | 8/1993 | Ziegler | |
| 5,268,166 A | 12/1993 | Barnett | |
| 5,273,214 A | 12/1993 | Huffstutler | |
| 5,299,743 A | 4/1994 | Sieth | |
| 5,302,378 A | 4/1994 | Crotty | |
| 5,397,394 A | 3/1995 | Orr | |
| 5,456,211 A | 10/1995 | Stevenson | |
| 5,460,192 A * | 10/1995 | McClain | 132/333 |
| 5,494,674 A | 2/1996 | Barnett | |
| 5,512,278 A | 4/1996 | Mundschenk | |
| 5,545,399 A | 8/1996 | Lee et al. | |
| 5,548,703 A * | 8/1996 | Berry et al. | 715/853 |
| 5,567,420 A | 10/1996 | McEleney | |
| 5,574,965 A * | 11/1996 | Welmer | 725/151 |
| 5,603,923 A | 2/1997 | Robinson | |
| 5,662,890 A | 9/1997 | Punto et al. | |
| 5,664,593 A | 9/1997 | McClain | |
| 5,700,452 A | 12/1997 | Deckner et al. | |
| 5,773,014 A | 6/1998 | Perrier | |
| 5,880,314 A | 3/1999 | Shinomiya | |
| 5,922,333 A | 7/1999 | Laughlin | |
| 6,117,118 A | 9/2000 | Laughlin | |
| 6,199,557 B1 * | 3/2001 | Laughlin | 132/200 |
| 6,214,322 B1 | 4/2001 | Castro | |
| 6,231,837 B1 | 5/2001 | Stroud | |
| 6,251,374 B1 | 6/2001 | Laughlin | |
| 6,298,862 B1 | 10/2001 | Laughlin | |
| 6,305,384 B2 | 10/2001 | Laughlin | |
| 6,357,845 B1 * | 3/2002 | Kuwabara et al. | 347/3 |
| 6,387,081 B1 * | 5/2002 | Cooper | 604/289 |
| 6,416,747 B1 | 7/2002 | Laughlin | |
| 6,421,180 B1 | 7/2002 | Montgomery | |
| 6,431,180 B2 | 8/2002 | Laughlin | |
| 6,439,243 B2 | 8/2002 | Laughlin | |
| 6,443,164 B1 | 9/2002 | Parker | |
| 6,446,635 B2 | 9/2002 | Laughlin | |
| 6,468,508 B1 | 10/2002 | Laughlin | |
| 6,474,343 B2 | 11/2002 | Laughlin | |
| 6,554,208 B1 | 4/2003 | Venuto, Sr. | |
| 6,656,455 B2 | 12/2003 | Laughlin | |
| 6,782,893 B2 | 8/2004 | Laughlin | |
| 6,799,580 B2 | 10/2004 | Laughlin | |
| 6,881,417 B1 * | 4/2005 | Laughlin | 424/401 |
| 2003/0146935 A1 * | 8/2003 | Adleman | 345/765 |

FOREIGN PATENT DOCUMENTS

| | | |
|---|---|---|
| DE | 3605807 | 8/1987 |
| GB | 9319158.8 | 3/1994 |

OTHER PUBLICATIONS

Dihydroxyacetone—Containing Sunless or Self-Tanning Lotions, Stanley B. Levy, Journal of the American Academy of Dermatology, 27: No. 6, pp. 898-993, 1992.

Erythropoietic Protoporphyria IV, Fusaro et al. (1970); Protection From Sunlight. Br. Med. J., vol. 1, pp. 730-731.

Formulating Effective Self-Tanners With DHA, T. Kurz, Cosmetics and Toiletries, 109 No. 11, pp. 55-60, 1994.

Non-Carcinogenicity of Dihydroxyacetone by Skin Painting, Frank J. Akin and Edward Marlowe, Journal of Environmental Pathology and Toxicology, 5: No. 5, pp. 349-351, 1984.

Persistence of Skin Color and Fluorescence After Treatment with Dihydroxacetone, J.A. Johnson & R.M. Fusaro, Dermatology 188: p. 247, 1994.

Photoprotection of Patients Sensitive to Short and/or Long Ultraviolet Light With Dihydroxyacetone/Naphtholquinone. Fusaro et al. (1974). Dermatologica, vol. 148, pp. 224-227.

Protection Against Light Sensitivity With Dihydroxyacetone/Naphthoquinone. Fusaro et al. (1992). Int. J. Dermato, vol. 11 pp. 67-70.

Protection Against Long UV Light With Dihydroxyacetone/Naphthoquinone. Johnson et al. (1973) Dermatologica, vol. 47, pp. 104-108.

Spray Application Processes, Binks Training Division, TD49-2R-4, Aug. 1995.

Sunlight Protection in Normal Skin. Fusaro et al; (1966). Archives of Dermatology, vol. 93, pp. 106-111 (Jan. 1966).

Sunlight Protection in Patients With Chlorpromazine Light Sensitivity. Fusaro et al. (1971). Int. J. Dermato, vol. 10, pp. 198-200.

Theory and Practice of Artificial Tanning Literature & Patent Survey, E. Futterer, Cosmetics and Perfumes, 88: No. 8 pp. 31-33 1973.

* cited by examiner

CHEMICALLY TANNING HUMAN SKIN

CROSS-REFERENCE TO RELATED APPLICATION

This application is a continuation of U.S. patent application Ser. No. 09/595,787 entitled Device and Method that Generates a Fog Capable of Altering the Color of Human Skin, also by Waters, et al. filed on Jun. 16, 2000, now U.S. Pat. No. 6,802,830.

TECHNICAL FIELD OF THE INVENTION

The present invention relates to devices and methods for generating a fog in a closed chamber, and more particularly to devices and methods for generating a fog that is capable of altering the color of human skin.

STATEMENT OF A PROBLEM ADDRESSED BY THIS INVENTION

Interpretation Considerations

This section describes the technical field in more detail, and discusses problems encountered in the technical field. This section does not describe prior art as defined for purposes of anticipation or obviousness under 35 U.S.C. section 102 or 35 U.S.C. section 103. Thus, nothing stated in the Problem Statement is to be construed as prior art.

Discussion

For decades, a tan has been associated with good health, a nice appearance, and general well being. Health can be enhanced by tanning. For example, vitamins D and, C, and E are all generated by a person's body when that person is exposed to the sun. In fact, phrases such as "healthy glow" have entered the modern lexicon. Furthermore, many people who tan regularly report that it makes them feel rejuvenated, relaxed, and calm. Unfortunately, tanning with ultraviolet rays has drawbacks.

For example, most people associate skin cancer with ultraviolet ray exposure. Furthermore, exposure to ultraviolet rays has been associated with premature skin wrinkling, as well as cell damage which can result in dry skin and the loss of melanin. Of course, anyone who has spent a day at the beach or a lake is familiar with the fact that ultraviolet radiation exposure causes sunburns. Fortunately, devices exist that minimize exposure to ultraviolet radiation while providing a tan.

For example, since not all ultraviolet radiation is created equal, some modern tanning units use cobalt lamps to reduce a person's exposure to harmful ultraviolet (UV) radiation (beta rays), while allowing that person to be exposed to the proper UV rays to generate a tan (alpha rays). This allows a person to become darker while reducing their exposure to harmful ultraviolet radiation significantly. However, manufacturing and using these devices is prohibitively expensive.

In addition, many people use suntan lotions which have SPF ratings that indicate that the lotions block ultraviolet radiation, and thus prevent damage by ultraviolet light. Furthermore, recover products exist that provide vitamins, minerals and moisturizers to skin which has been exposed to ultraviolet radiation. Unfortunately, these products are often expensive, difficult to apply and are easily ignored or forgotten just after exposure to UV light, which is just when they are most needed. Furthermore, none of these products provide 100 percent protection from ultraviolet radiation.

Recently, to provide a darker and more healthy looking skin complexion, it has become popular to use tanning lotions and sprays that darken skin (self-bronzing applications). For example, one device uses a carwash-like spraying apparatus to coat one side of a person at a time by either moving a spray up and down or side to side across the person. These applications have the benefit of giving a person a healthy looking tan while not requiring that person to be exposed to ultraviolet radiation. Unfortunately, these spray applicators have several disadvantages.

For example, by spraying a person one side at a time, that side that is sprayed first will have a longer exposure to the tanning spray that the side of the person which is last exposed. In addition, there is an overlap as the person turns and the sprayers hit an area more than once, resulting in a buildup of excess tanning spray at different locations on a person.

Furthermore, the use of a sprayer that sprays a person one side at a time results in a long and tedious process—a process in which the person being sprayed typically must close their eyes and hold their breather until the process is complete (which may take as long as half a minute or more). The result is that these devices are uncomfortable for a person to use, and can create uneven tanning with noticeable dark areas that can look quite strange.

However, it is desirable to provide a device which can apply a tanning solution to a person without these disadvantages. This would be particularly advantageous to persons who have been diagnosed with skin cancer and allow them to obtain a healthy looking tan without UV exposure. Therefore, there exist the need for a device and method for applying a tanning solution quickly and evenly.

BRIEF DESCRIPTION OF THE DRAWINGS

Various aspects of the invention, as well as an embodiment, are better understood by reference to the following detailed description. To better understand the invention, the detailed description should be read in conjunction with the drawings in which.

EXEMPLARY EMBODIMENT OF A BEST MODE

Interpretation Considerations

Figure 1:
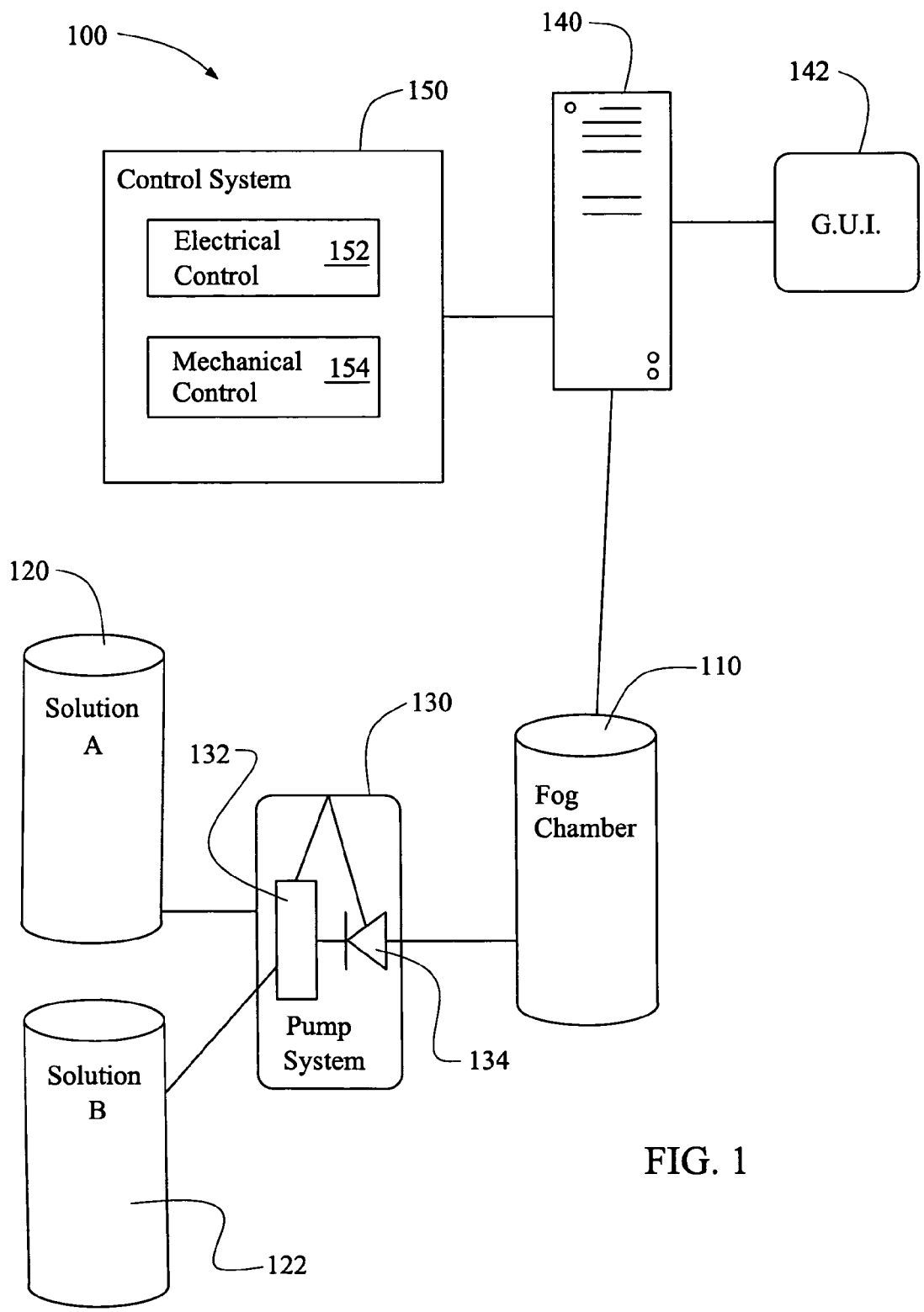
FIG. 1 illustrates some component that may be provided in one embodiment of a tanning system.

When reading this section (An Exemplary Embodiment of a Best Mode, which describes an exemplary embodiment of the best mode of the invention, hereinafter "exemplary embodiment"), one should keep in mind several points. First, the following exemplary embodiment is what the inventor believes to be the best mode for practicing the invention at the time this patent was filed. Thus, since one of ordinary skill in the art may recognize from the following exemplary embodiment that substantially equivalent structures or substantially equivalent acts may be used to achieve the same results in exactly the same way, or to achieve the same results in a not dissimilar way, the following exemplary embodiment should not be interpreted as limiting the invention to one embodiment.

Likewise, individual aspects (sometimes called species) of the invention are provided as examples, and, accordingly, one of ordinary skill in the art may recognize from a following exemplary structure (or a following exemplary act) that a substantially equivalent structure or substantially equivalent act may be used to either achieve the same results in substantially the same way, or to achieve the same results in a not dissimilar way.

Accordingly, the discussion of a species (or a specific item) invokes the genus (the class of items) to which that species belongs as well as related species in that genus. Likewise, the recitation of a genus invokes the species known in the art. Furthermore, it is recognized that as technology develops, a number of additional alternatives to achieve an aspect of the invention may arise. Such advances are hereby incorporated within their respective genus, and should be recognized as being functionally equivalent or structurally equivalent to the aspect shown or described.

Second, the only essential aspects of the invention are identified by the claims. Thus, aspects of the invention, including elements, acts, functions, and relationships (shown or described) should not be interpreted as being essential unless they are explicitly described and identified as being essential. Third, a function or an act should be interpreted as incorporating all modes of doing that function or act, unless otherwise explicitly stated (for example, one recognizes that "tacking" may be done by nailing, stapling, gluing, hot gunning, riveting, etc., and so a use of the word tacking invokes stapling, gluing, etc., and all other modes of that word and similar words, such as "attaching").

Fourth, unless explicitly stated otherwise, conjunctive words (such as "or", "and", "including", or "comprising" for example) should be interpreted in the inclusive, not the exclusive, sense. Fifth, the words "means" and "step" are provided to facilitate the reader's understanding of the invention and do not mean "means" or "step" as defined in §112, paragraph 6 of 35 U.S.C., unless used as "means for —functioning—" or "step for —functioning—" in the Claims section. Sixth, the invention is also described in view of the Festo decisions, and, in that regard, the claims and the invention incorporate equivalents known, unknown, foreseeable, and unforeseeable. Seventh, of course, the discussions and definitions are provided for clarification purposes and are not limiting, and the language and each word used in the invention should be given the ordinary interpretation of the language and the word, unless indicated otherwise. It should be noted in the following discussion that acts with like names are performed in like manners, unless otherwise stated.

Description of the Drawings

In one embodiment, the invention provides a tanning system. FIG. 1 illustrates components that may be provided in one embodiment of a tanning system 100. In the tanning system 100 a graphical user interface (GUI) 142 is provided so that an operator of tanning system 100 may select and adjust various settings of the tanning system. For example, by using the graphical user interface 142, one may select a predetermined pressure, a predetermined program which varies pressures, a tanning solution, a combination of tanning solutions, a combination of a tanning solution and a moisturizer, or a temperature at which any of these is delivered into a fog chamber 110. Accordingly, settings selected at the graphical user interface are supplied to a computer 140. Alternatively, any of the settings described as being selected at the graphical user interface 142 may be selected by a user within the fog chamber 110 via a control pane (not shown).

The computer 140 may be any comprising platform capable of executing a computer code, which enables the tanning system 100. For example, the computer 140 could be a personal computer (PC), a laptop, or a specific use-computing device. Preferably, the computer 140 sores and executes a tanning system algorithm (discussed later).

The computer 140 is coupled to a control system 150. The control system 150 typically houses an electrical control subsystem 152, and a mechanical control subsystem 154. The control system 150 opens and closes valves within a pump system 130 so as to implement the settings directed at the graphical user interface 142, or by a user at the control panel. Accordingly, the electrical control subsystem 152 is generally controlled by the computer 140 so as to actuate the mechanical control subsystem 154.

The mechanical subsystem 154 implements the opening and closing of valves within the pump system 130, such as the flow valve 134, and the valve(s) in the pump 132 which controls the flow of solutions into the pump system 130. It should be noted that although the control system 150 appears in FIG. 1 to be rather larger, the control system 150 is typically a quite small device.

The control system 150 is thus coupled to the pump system 130 so as to control the valves therein. Furthermore, the pump system 130 accepts solution from a first solution container 120, containing a Solution a, and a second solution 122 containing a Solution B. The Solution A and the Solution B may be tanning solutions or moisturizers or other solutions or liquids to be delivered to the fog chamber 110. The pump 132 places the incoming solutions under pressure, and preferably places the solutions at predetermined pressure.

For example, if a liquid with water-like consistency is pumped, then the predetermined pressure may be between 450 and 550 psi, and is preferably 500 psi. Similarly, if a lotion is pumped, the predetermined pressure may be between 550 and 650 psi, with a preferred predetermined pressure of 600 psi. Likewise, the flow valve 134 is opened and closed by the control system 150 so as to allow the tanning solution which exits the pump 132 at the predetermined pressure to pass into the fog chamber 110.

Figure 2:
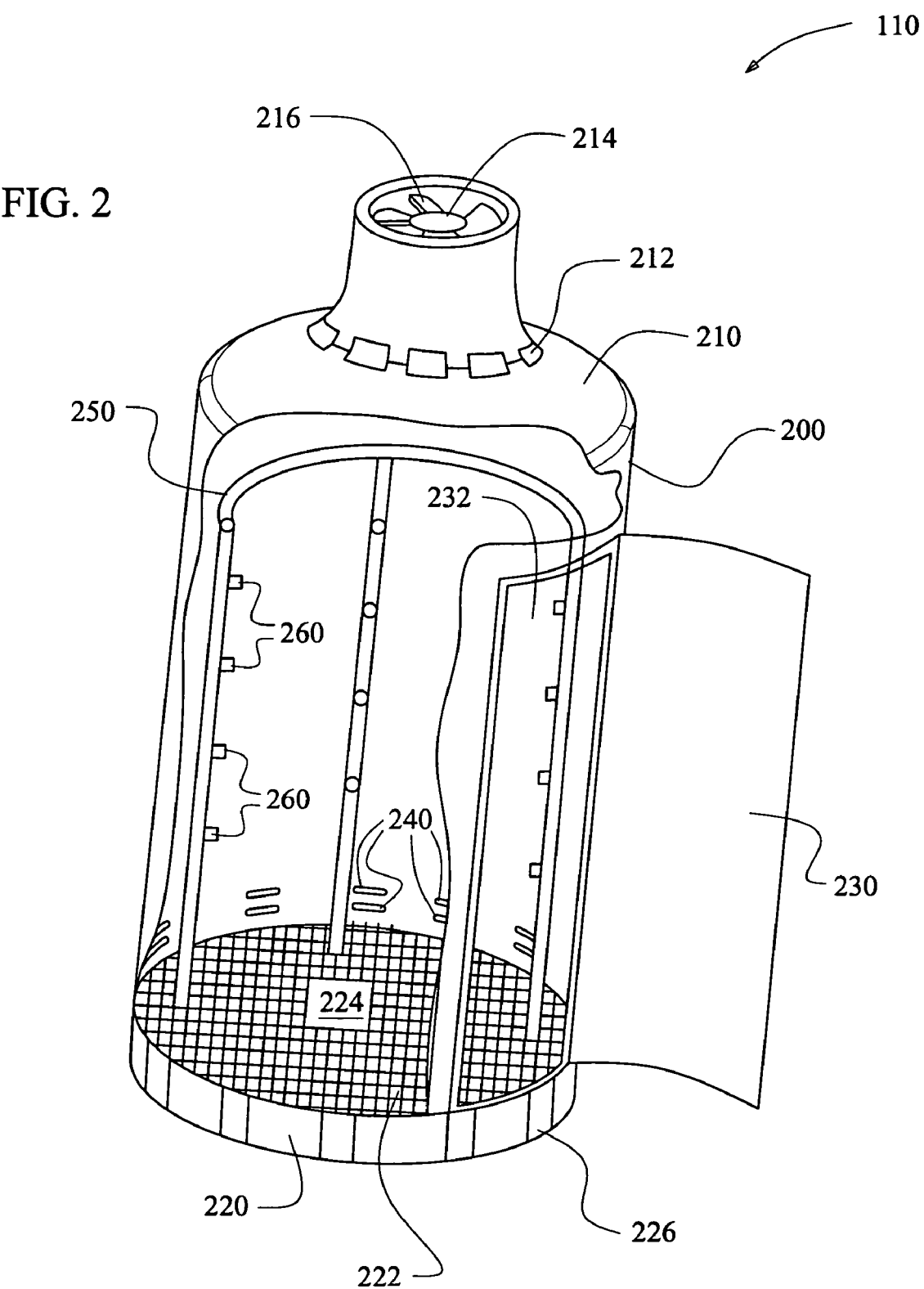
FIG. 2 illustrates one embodiment of a fog chamber.

A fog chamber 110 is a generally enclosed housing used to encapsulate a fog about a person being tanned, and to maintain the fog at a predetermined density. FIG. 2 illustrates one embodiment of a fog chamber 110. The fog chamber 110 is generally comprised of an outer shell 200, a hood 210 and a floor 220. The hood 210 is preferably a plastic of fiberglass form capable of supporting a lighting system 212 as well as a fan motor 214. The fan motor 214 drives fan blades 216 to vent and evacuate the chamber.

Accordingly, during operation, the lighting system 212 provides lighting within the fog chamber 110. In addition, the fan motor 214 operates at a low speed during the fogging process to provide ventilation within the fog chamber 110, and at high speed to quickly evacuate the fog chamber 200 when the person being tanned has been exposed to the fog for a sufficient time.

The floor 220 includes a plurality of legs 226, which support a generally mesh-like floor piece 222 thereon. The floor piece 222 is elevated above the floor 220 in order to provide ventilation about the feet of the person being tanned. Furthermore, the floor piece 222 includes a standing platform 224 on which a person may stand without their feet being irritated by the floor piece 222. In addition, the generally mesh nature of the floor piece 222 allows condensation and excess fog to fall to the floor 220.

The outer shell 200 provides a door 230, which opens and shuts about a doorway 232 for providing access into the tanning chamber 110. The outer shell 200 like the hood 210 is preferably made of a fiberglass or a moldable plastic. Also provided within the outer shell 200 are a plurality of vents 240 for providing fresh air access into the fog chamber 110. Disposed within the outer shell 200 is a fluid frame 250, which provides tanning solution (or other liquid or lotion) to the fog chamber 110. The fluid frame is preferably constructed of ⅜" copper pipe and contains a plurality of nozzles 260 thereon.

Figure 3:
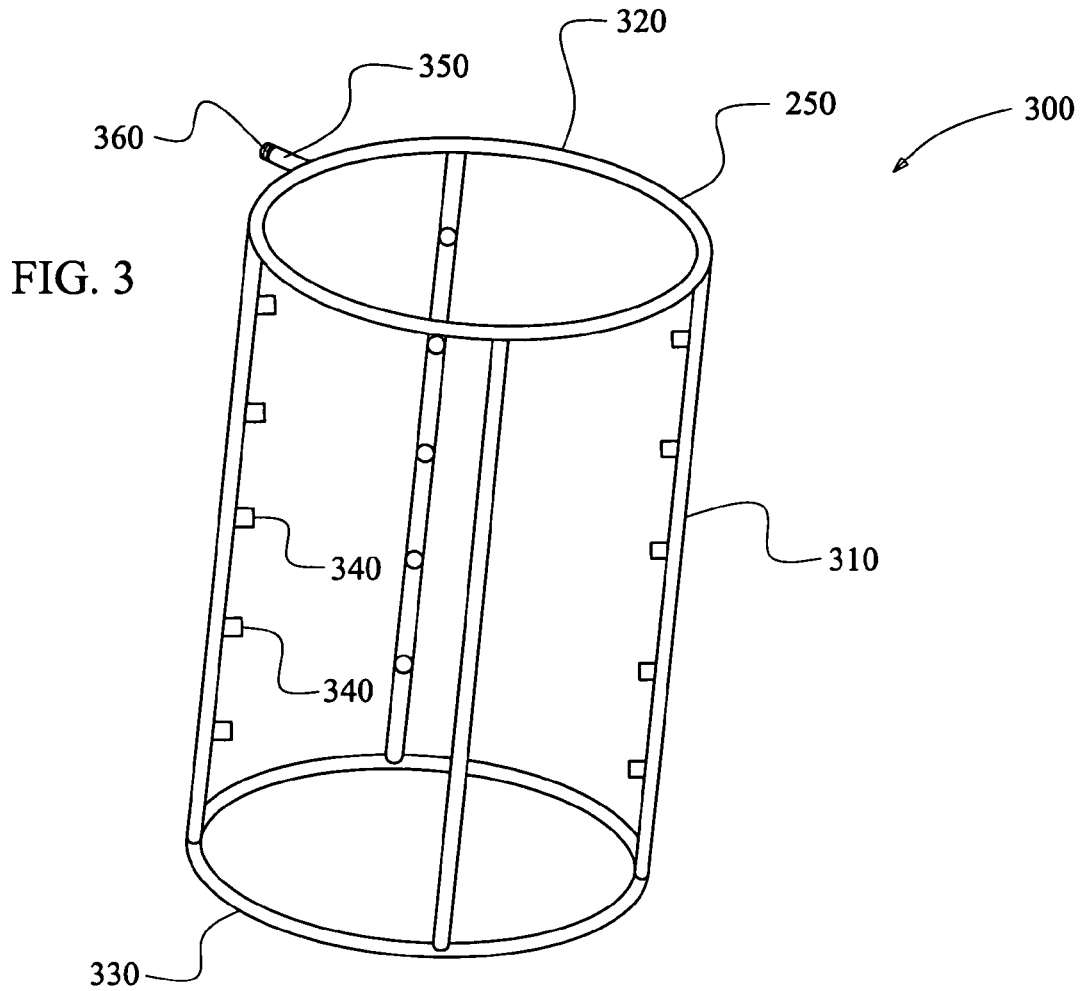
FIG. 3 illustrates a fluid frame system for use within a generally cylindrical outer shell, such as the outer shell.

Each fluid frame is customized to provide a generally uniform fog to a user within the fog chamber 110. Accordingly, the fluid frame, in operation, is generally disposed about the person being tanned. FIG. 3 illustrates a fluid frame 300 for use within a generally circular top frame piece 320, a generally circular bottom frame 330, and a plurality of vertical frame pieces 310. Each of the frame pieces 310, 320, 330, may be fluidly connected to a plurality of nozzles 340.

The number and location of the nozzles 340 is chosen based on the desire to produce a generally uniform fog within the area generally enclosed by the fluid frame 250. Furthermore, each nozzle 340 is pointed in a direction that supports the creation of a uniform fog within the fog chamber 110. Also coupled to the fluid frame 250 is an empty pipe 350, which brings the tanning solution (or tanning solution mixture) into the fluid frame 250. Controlling access of a fluid to the fluid frame 250 via the entry pipe 350 is an entry valve 360.

The entry valve 360 provides a user of the tanning system the ability to quickly turn the tanning system off should that user desire to do so. Accordingly, the entry valve 360 is typically coupled to the computer 140, or the control system 150. Alternatively, the entry valve 360 maybe directly mechanically turned on and off by an off switch (not shown) within the fog chamber.

Figure 4A:
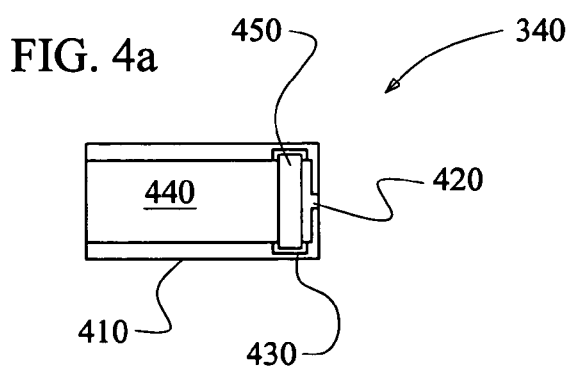
FIG. 4a illustrates a nozzle designed to produce a fog.

A nozzle capable of producing a fog is utilized by the invention. Accordingly, FIG. 4a illustrates a nozzle 340 designed to produce a fog. The nozzle 340 includes a generally cylindrical shell 410 having an orifice 420 at one end (the end the fog exits, the other end being attachable to the fluid frame) and maintaining a cylinder 440 therein. The orifice 420 is of a size, which enables the nozzle 340 to produce a fog, and is preferably between 0.005 and 0.0200 inches in diameter, and is preferably 0.012 inches in diameter. Furthermore, the nozzle 340 provides an annular indentation 430 capable of supporting a disk fan 450 therein.

Figure 4B:
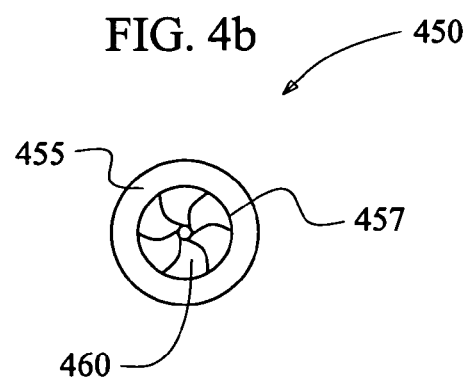
FIG. 4b illustrates one embodiment of the disk fan.

FIG. 4b illustrates one embodiment of the disk fan 450. The disk fan 450 provides a generally circular outer ring 455, which supports a plurality of fan blades 460 within its inner radius 457. Referring to FIGS. 4a and 4b, when a fluid is passed in the chamber 440, and through the orifice 420, the flow of the fluid causes the fan blades 460 to turn the disk fan 450 so that the disk fan 450 rotates rapidly. The rapid spinning of the disk fan 450 causes a more even and uniform dispersion of a fog within the fog chamber 110. This provides the additional advantage of preventing a user of the tanning system from being irritated by a direct spray.

Exemplary Method

Figure 5:
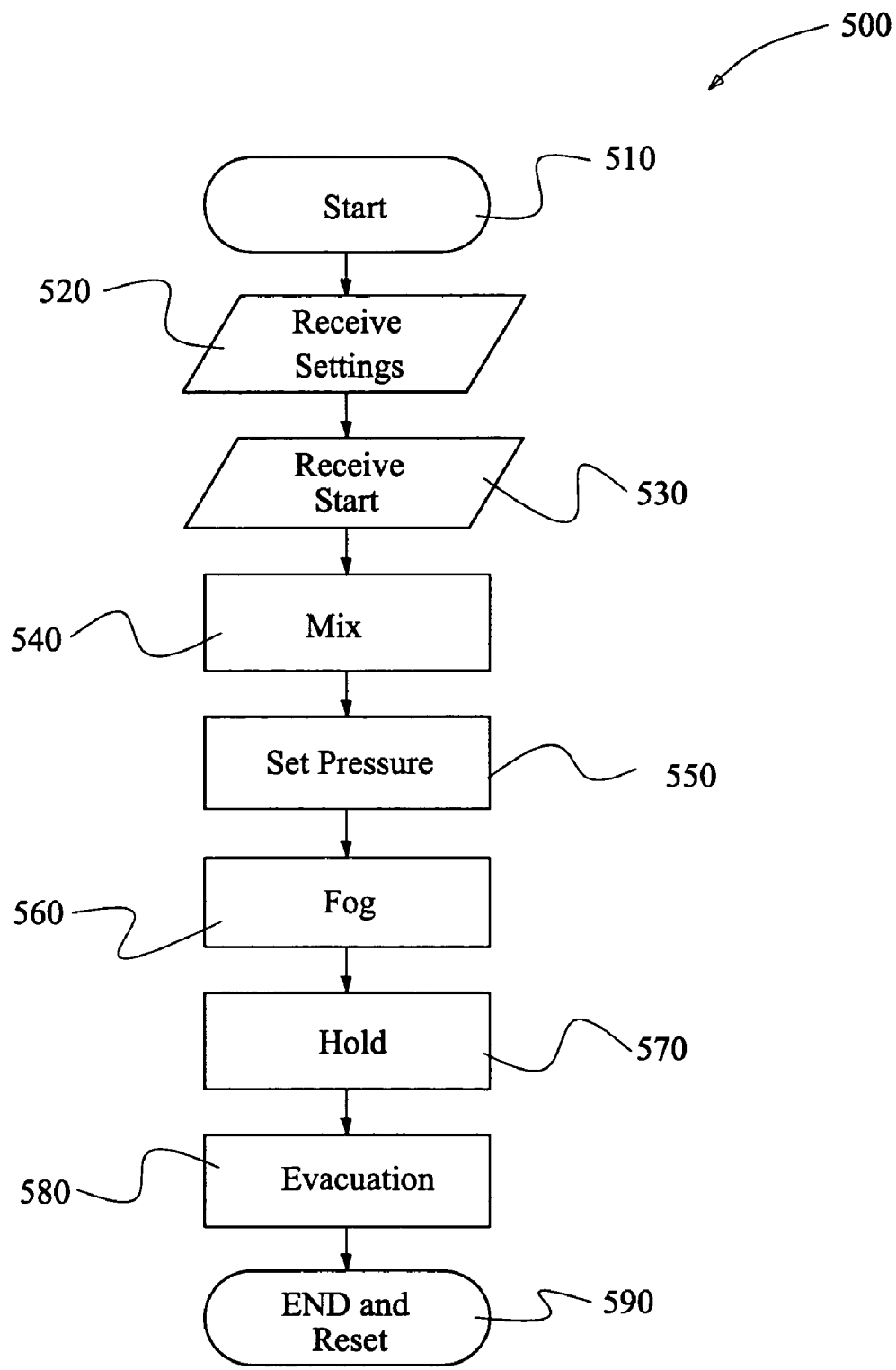
FIG. 5 is a flow chart of a tanning algorithm.

One embodiment of a method according to the invention may be understood as a tanning algorithm 500. FIG. 5 is a flow chart of a tanning algorithm 500. First, in a start act 510, the tanning system algorithm 500 is loaded into a computer memory and performs all of the procedures needed to initialize a control system or a pump system and may heat any fluids to a predetermined temperature. Then, in a receive settings act 520, the settings selected at either the graphical user interface or a user control panel within the fog chamber are received by the tanning system algorithm 500.

The settings may include a selection of a temperature for a tanning solution, a predetermined fogging program which implements variable fog densities for predetermined times, a selected time period for exposure to a fog, a selected fog density, or settings. Next, in a receive start act 530, the tanning system algorithm 500 receives an indication that the fogging process is to begin. The receive start act 530 may be initiated by a user within the fog chamber, by a person at a graphical user interface, or automatically via computer program.

The tanning system algorithm 500 next proceeds to a mix act 540 in which any tanning solution mixtures selected are either mixed prior to being placed in a pump, or either set so that they may be mixed by a pump. Then, in a set pressure act 550, the tanning solution (or tanning solution mixture, but collectively "tanning solution") is pumped to a user-selected pressure. Next, the fog act 560 is implemented by the opening of valves, which allow the tanning solution to flow into a fog chamber. Also within the fog act 560 a fog is produced within the fog chamber 110. In a hold act 570 the fog density is controlled and held at a predetermined density, which is either user, selected or selected by a program, which was selected by the user or the person operating a graphical user interface. Preferably, during the hold act 570, a fan is operating at a low speed in order to vent air into the chamber at a predetermined rate.

The fog evacuated from the fog chamber 110 in an evacuation act 580. Preferably, the evacuation act 580 is very fast, and preferably almost instantaneous. Then, the tanning system algorithm 500 continues to end and reset act 590. The end and reset act 590 terminates the execution of the tanning system algorithm 500 and resets the pre-pump system and the control system so that another user may enter and use the fog chamber 110.

Sometimes methods of the invention may be practiced by placing the invention on a computer-readable medium. Computer-readable mediums include passive data storage, such as a random access memory (RAM) as well as semi-permanent data storage such as a compact disk read only memory (CD-ROM). In addition, the invention may be embodied in the RAM of a computer and effectively transform a standard computer into a new specific computing machine, such as a tanning system.

Of course, it should be understood that the order of the acts of the algorithms discussed herein may be accomplished in different order depending on the preferences of those skilled in the art, and such acts may be accomplished as software. Furthermore, though the invention has been described with respect to a specific preferred embodiment, many variations and modifications will become apparent to those skilled in the art upon reading the present application. It is therefore the intention that the appended claims and their equivalents be interpreted as broadly as possible in view of the prior art to include all such variations and modifications.

We claim:

1. A system that generates a fog with a tanning solution, comprising:
    an outer shell; a stationary fluid frame disposed within the outer shell; and at least one stationary nozzle in the fog chamber, and in fluid communication with the fluid frame, the stationary nozzle capable of turning a tanning fluid into a fog by passing the fluid through an orifice; and a user control panel disposed within the outer shell, the user control panel configured for selection of a tanning solution by a user from a plurality of tanning solution choices.

* * * * *